United States Patent
Dubois et al.

(10) Patent No.: US 6,668,654 B2
(45) Date of Patent: Dec. 30, 2003

(54) METHOD AND APPARATUS FOR GENERATING SPECIFIC FREQUENCY RESPONSE FOR ULTRASOUND TESTING

(75) Inventors: Marc Dubois, Clifton Park, NY (US); Peter W. Lorraine, Niskayuna, NY (US); Robert J. Filkins, Niskayuna, NY (US)

(73) Assignee: Lockheed Martin Corporation, Bethesda, MD (US)

(*) Notice: Subject to any disclaimer, the term of this patent is extended or adjusted under 35 U.S.C. 154(b) by 0 days.

(21) Appl. No.: 09/930,015

(22) Filed: Aug. 15, 2001

(65) Prior Publication Data

US 2003/0033882 A1 Feb. 20, 2003

(51) Int. Cl.[7] .............................................. G01N 29/04
(52) U.S. Cl. .......................... 73/643; 73/602; 356/502; 356/503
(58) Field of Search ................... 73/643, 602; 356/503, 356/502, 499, 432

(56) References Cited

U.S. PATENT DOCUMENTS

| | | | | |
|---|---|---|---|---|
| 3,978,713 A | * | 9/1976 | Penney | 73/627 |
| 4,144,767 A | * | 3/1979 | Kaule et al. | 73/643 |
| 4,169,662 A | | 10/1979 | Kaule et al. | 350/358 |
| 4,246,793 A | * | 1/1981 | Fairand et al. | 73/628 |
| 4,567,769 A | | 2/1986 | Barkhoudarian | 73/643 |
| 4,674,332 A | * | 6/1987 | Pace et al. | 73/597 |
| 5,381,695 A | * | 1/1995 | Payne et al. | 73/643 |
| 5,573,497 A | | 11/1996 | Chapelon | 601/1 |
| 5,621,173 A | | 4/1997 | Knorr | 73/610 |
| 5,738,635 A | | 4/1998 | Chapelon et al. | 601/2 |
| 5,909,279 A | | 6/1999 | Pepper et al. | 356/345 |
| 6,041,020 A | | 3/2000 | Caron et al. | 367/149 |
| 6,057,927 A | | 5/2000 | Lévesque et al. | 356/432 T |
| 6,128,081 A | | 10/2000 | White et al. | 356/357 |
| 6,181,431 B1 | | 1/2001 | Siu | 356/502 |
| 6,227,036 B1 | | 5/2001 | Yonak et al. | 73/40.5 A |
| 6,234,023 B1 | * | 5/2001 | Collins et al. | 73/597 |
| 6,486,962 B1 | * | 11/2002 | Telschow et al. | 356/503 |
| 2002/0066318 A1 | * | 6/2002 | Dubois et al. | 73/579 |

FOREIGN PATENT DOCUMENTS

| | | |
|---|---|---|
| EP | 0097473 A1 | 4/1985 |
| EP | 0400770 A2 | 12/1990 |
| EP | 0565570 A1 | 12/1992 |
| EP | 0634077 A1 | 10/1993 |
| EP | 0967913 A1 | 9/1998 |

OTHER PUBLICATIONS

Yves H. Berthelot, "Thermoacoustic Generation of Narrow–Band Signals with High Repetition Rate Pulsed Layers," School of Mechanical Engineering, Georgia Institute of Technology, J. Acous. Soc. Am. 85 (3), Mar. 1989, pp. 1173–1181.

B.R. Tittman, et al. "Laser–Based Ultrasonics on Gr/Epoxy Composite," Plenum Publishing Corp., Sep. 1990, pp. 229–238.

James W. Wagner, et al. "Generation of Ultrasound by Repetitively Q–switching a Pulsed Nd:YAG Laser," Applied Optics, vol. 27, No. 22, Nov. 1988, pp. 4696–4700.

R. Pierce, et al. "Temporal Modulation of a Laser Source for the Generation of Ultrasonic Waves," Ultrasonics, vol. 33, No. 2, 1995, pp. 133–136.

* cited by examiner

Primary Examiner—Hezron Williams
Assistant Examiner—Rose M. Miller
(74) Attorney, Agent, or Firm—Koestner Bertani LLP (57) ABSTRACT

A system and method for testing a physical attribute of a manufactured object that includes a laser generator and pulse generator that generate a plurality of Dirac-like pulses. The pulses, directed at an object, cause a sonic signal to be initiated indicative of the physical attribute of the manufactured object, and are detected. The system also controls the width of the Dirac-like pulses and time separation between pulses. A display may also be used to present the detected signal or physical attribute. The Dirac-like pulses are structured to produce a particular output in the manufactured object. The Dirac-like pulses may be altered dynamically in the presence of deviations from the expected output. One embodiment of the Dirac-like pulses is a series of pulses with pulse widths less than 20% a time separation between successive pulses.

20 Claims, 11 Drawing Sheets

METHOD AND APPARATUS FOR GENERATING SPECIFIC FREQUENCY RESPONSE FOR ULTRASOUND TESTING

BACKGROUND

1. Field of the Invention

The present invention generally relates to the testing of manufactured parts for defects. In particular, the present invention relates to laser ultrasound testing methods for testing composite materials and parts made of those materials wherein a series of narrow laser pulses is used to enhance or optimize a resulting ultrasonic signal in the tested material.

2. Description of Prior Art

Laser ultrasound testing methods are non-invasive, generally non-destructive, techniques used to measure various features of materials or parts. These features may include layer thickness, cracks, delamination, voids, disbonds, foreign inclusions, fiber fractions, and fiber orientation. The features may influence a given material's qualities and performance in given applications. Each application places unique demands on the material's qualities including the need for differing strength, flexibility, thermal properties, cost, or ultraviolet radiation resistance.

Many techniques are available such as visual, radiographic, thermographic, acoustic-emission, optical, vibrational and ultrasonic methods. Visual techniques examine the surface of an object and infer internal features. Radiographic techniques such as X-ray and gamma-ray techniques detect variations in absorption to determine features. Thermographic techniques observe surface temperatures during heating to determine variations in the materials. Acoustic methods utilize acoustic noise caused by microscopic failures in the material. Optical techniques seek variations in deformations upon stress. Vibrational inspection uses local pulse excitation to exploit the sonic properties of the component. Ultrasonic methods include laser induced and transducer induced techniques and detect features of objects or materials by exploiting differences in acoustic impedances between features.

Laser ultrasound techniques use a laser pulse which when directed at an object causes thermal expansion in a small region. The thermal expansion causes ultrasonic waves which are then measured by a detector and converted into information about the features of the object. The laser pulse may be generated by several lasers. Various types of lasers used include carbon dioxide lasers and a Nd:YAG lasers. The object that is to be tested may be composed of metal, composite materials, ceramic material, or any other type of material. The detector may be a transducer on the surface of the object, a laser interferometer directed at the object, or a gas-coupled laser acoustic detector.

The measured ultrasonic signals are analyzed to reconstruct physical attributes of the object that have a position or location with the object and a size. A combination of the optical penetration depth in the material given the generation-laser optical wavelength and of the temporal profile or pulse width of the generation-laser pulse dictate the frequency content of the laser-generated ultrasonic waves.

One problem associated with many typical ultrasound detectors is a poor signal-to-noise ratio (SNR) in the resulting signals. SNR is proportional to the amplitude of the sonic wave and inversely proportional to the square root of the bandwidth of the sonic wave. Many typical generation techniques produce low amplitude and/or broad bandwidth ultrasonic signals. Either of these conditions lead to an increased SNR and limits the quality of data acquired through such ultrasonic testing. In combination, these effects drastically reduce the ability to detect features in the tested object. The poor SNR in typical systems leads to poor resolution in the resulting analysis. Smaller features like fractures may be difficult to detect with poor resolution. With the lower SNR of the typical systems, these smaller size features may go unnoticed.

When testing fails to detect these smaller features, these features may ultimately yield many problems, such as poor material performance or catastrophic failure of the part. When testing parts used in the airline industry, failure to detect flaws may lead to safety problems and costly accidents.

As such, many typical laser ultrasonic testing devices suffer from low quality measurements caused by low amplitude and high frequency bandwidth. Many other problems and disadvantages of the prior art will become apparent to one skilled in the art after comparing such prior art with the present invention as described herein.

SUMMARY OF THE INVENTION

Aspects of the invention are found in a system for testing physical attributes of a manufactured object. The system has a coherent electromagnetic energy generator coupled to a pulse generator. In combination, these produce a plurality of coherent electromagnetic energy pulses. The plurality of pulses generally have pulse widths of less than 20% the time separation between successive pulses.

The pulses are directed at the manufactured object and impart energy to the manufactured object. The imparted energy then initiates a sonic energy signal in the manufactured object. A detection system detects this sonic energy signal emitted by the manufactured object.

Still, other aspects of the invention include the systems described above where a controlling circuitry may define and/or control the pulse widths of the coherent electromagnetic energy pulses and the time separation between successive pulses. Further, the controlling circuitry may use the physical attribute of the manufactured object or the features of the coherent electromagnetic energy pulses to determine proper or optimal pulse widths and time separation between pulses.

The detection system of the systems described above may be various in nature. They can be transducers, a laser interferometer, an electromagnetic transducer (EMAT), or a gas-coupled laser acoustic detector, to name but a few.

Another aspect of the invention is a method for testing physical attributes of a manufactured object. The method comprises generating a plurality of coherent electromagnetic energy pulses. These pulses have pulse widths less than 20% the time separation between successive pulses. The method calls for directing the pulses at a manufactured object where the pulses impart energy on or in the manufactured objects. This energy initiates a sonic energy signal and the sonic energy signal is detected.

Further aspects of the invention add to the above methods a step where the pulse widths of the coherent electromagnetic energy pulses and the time separation between pulses may be defined and/or controlled. Further, the pulse widths of the coherent electromagnetic energy pulses and the time separation between successive pulses may be defined by the physical attribute of the manufactured object or the features of the coherent electromagnetic energy pulses. The pulses may be defined to generate a specific sonic response in the object.

An exemplary embodiment of the system for testing a physical attribute of a manufactured object may be found in a laser ultrasound testing system. This laser ultrasound testing system has a laser generator, a pulse generator attached to the laser generator, and a sonic energy detection system. The pulse generator produces a plurality of narrow width pulses which are directed at the manufactured object.

The pulses impart energy on or in the manufactured object. This energy initiates a sonic energy signal which is detected by the detection system.

In this case, a plurality of narrow width pulses can be defined as a plurality of laser pulses separated from one another by a time separation between a first pulse and a successive pulse. The temporal profile of the successive pulse is less than 20% the time separation between pulses. The plurality of narrow width pulses may be further described as Dirac-like pulses.

As such, a system for testing manufactured objects using laser ultrasound is described. Other aspects, advantages, and novel features of the present invention will become apparent from the detailed description of the invention when considered in conjunction with the accompanying drawings.

BRIEF DESCRIPTION OF THE DRAWINGS

FIGS. 3a and 3b are graphs comparing the sonic amplitude signals produced by various pulses or series of pulses as a function of the sonic frequency.

FIG. 10 is a schematic diagram depicting a further exemplary embodiment of the apparatus for producing the pulses of coherent electromagnetic energy of FIG. 2.

DETAILED DESCRIPTION OF THE PREFERRED EMBODIMENT

Figure 1:
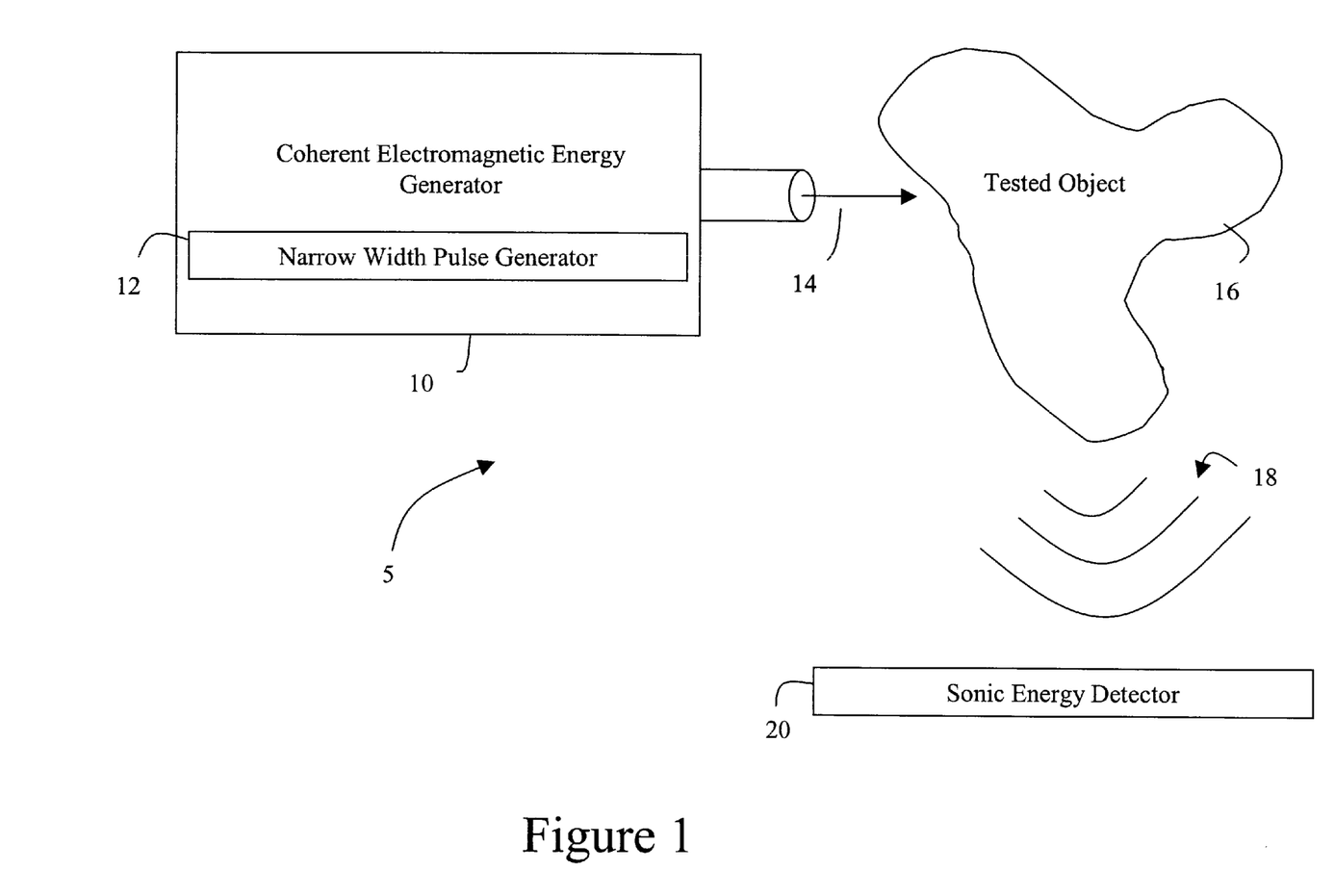
FIG. 1 is a schematic block diagram of a system for testing physical attributes of a manufactured object according to the invention.

FIG. 1 is a schematic block diagram of a system for testing physical attributes of a manufactured object according to the invention. A testing system has a coherent electromagnetic energy generator 10 coupled to a pulse generator 12. The pulse generator generates a plurality of narrow pulses of coherent electromagnetic energy 14. The pulse or pulses have characteristic features. These features may include wavelength, frequency, power, beam projected shape, temporal profiles and energy amplitude. These pulses 14 are directed at a tested manufactured object 16.

The pulses 14 impart energy to the manufactured object 16. The energy creates a sonic energy signal 18 on or in the manufactured object 16. The sonic energy signal is representative of physical features of the manufactured object 16. A detector 20 detects the sonic energy signal 18 from the manufactured object. In this manner, information about the physical attributes of the manufactured object 16 is gleaned.

These attributes may include defects like delamination, voids, or foreign inclusions. Other attributes may include quality aspects like numbers of layers, thicknesses of layers, fiber fractions, fiber orientations, or porosity. As such, an inspection of various physical properties of the object may be performed through analysis of the generated energy.

The coherent electromagnetic energy generator 10 may be a laser. Such lasers may include ruby lasers, carbon lasers, or Nd:YAG lasers, to name a few or any other device that can produce electromagnetic pulsed energy like, but not limited to, an optical parametric oscillator.

The pulse generator may use one of several techniques to generate pulses. These techniques may include q-switching, mode-locking, or chirping, among others.

The sonic energy detector 20 may take various forms. These forms include a transducer, a laser interferometer, or a gas-coupled laser acoustic detector, to name a few.

Figure 2:
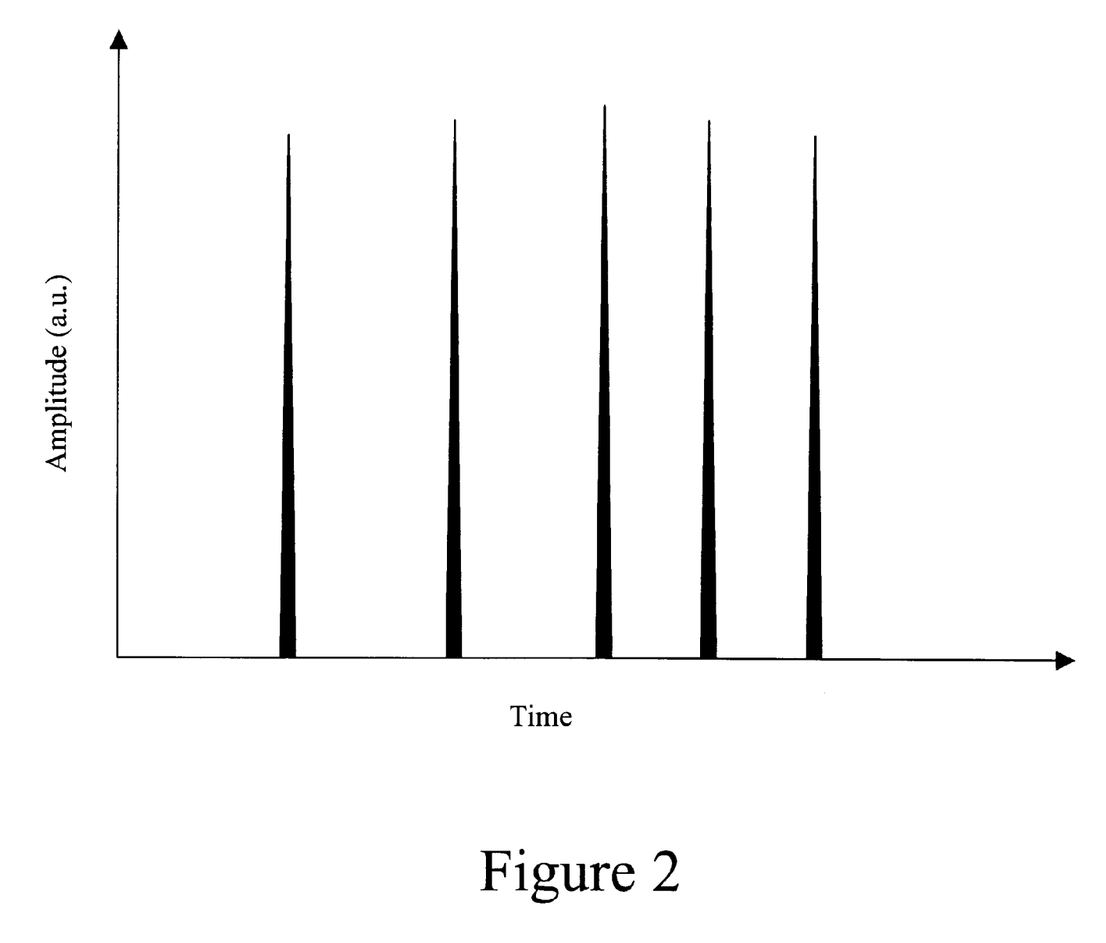
FIG. 2 is a time series graph of an exemplary series of extremely narrow width pulses of coherent electromagnetic energy that may be produced by the system of FIG. 1.

FIG. 2 is a time series graph of an exemplary series of narrow width pulses of coherent electromagnetic energy that may be produced by the system of FIG. 1. Narrow width pulses may be thought of as pulses having pulse widths of less than 20% of a time difference between the end of the preceding pulse and the beginning of the defined pulse. The pulse widths may, by way of example be 10%, 5%, 1% or less of the time separation between successive pulses. Such narrow width pulses may also be termed "Dirac-like" pulses.

Although the pulses are depicted as triangular spikes, these may be square waves, sinusoidal waves, or any other shape providing the width of the pulses match the above described definition of narrow width or Dirac-like pulses. Additionally, the pulses may be temporally spaced in various arrangements. For example, the pulses may be evenly spaced, unevenly spaced, or distributed in a specific pattern, in time, to name but a few.

Figure 3A:
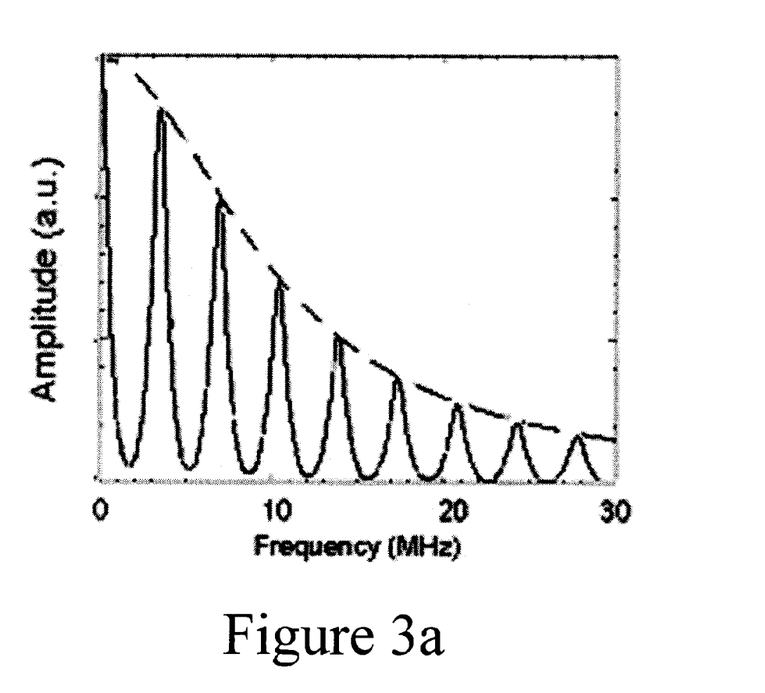
FIG. 3a is a graph of sonic amplitude signals produced by an extremely narrow width pulse (dashed line) and pulses like those of FIG. 2 (solid line).
Figure 3B:
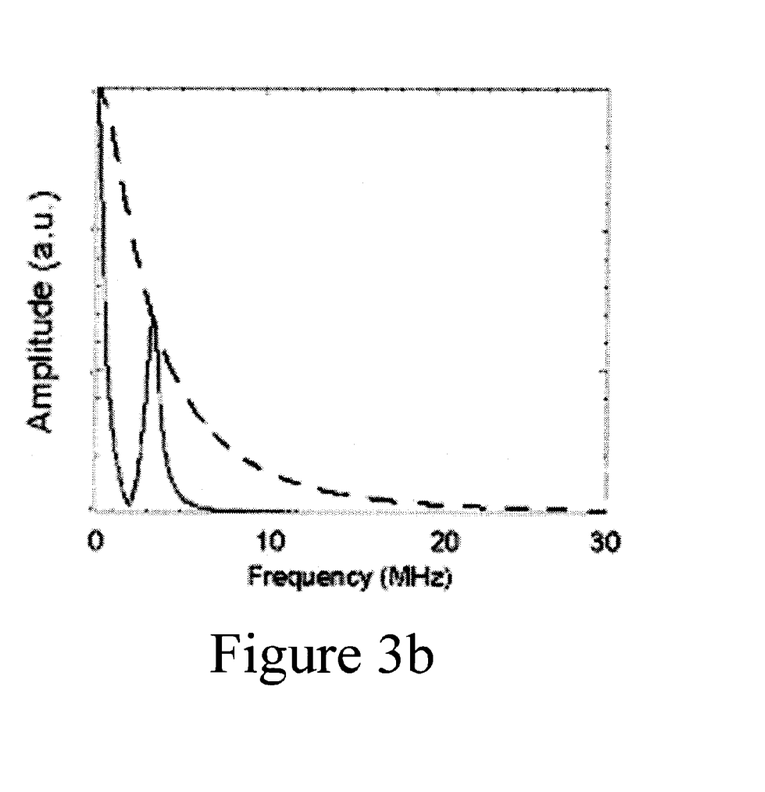
FIG. 3b is a time series graph of sonic energy signals produced by a laser tone-burst excitation (solid line) and by a single pulse having a width corresponding to one cycle of the tone-burst (dashed line).

FIGS. 3a and 3b are graphs comparing sonic amplitude signals produced by various pulses of coherent electromagnetic energy as a function of the sonic frequency. FIG. 3a shows exemplary sonic energy signals produced by one Dirac-like pulse or the pulses of coherent electromagnetic energy similar to that shown in FIG. 2. In FIG. 3a, the dashed line denotes an ultrasonic energy signal produced by a process using a single Dirac-like pulse of coherent electromagnetic energy. The solid line denotes an ultrasonic energy signal produced by a process using a series of Dirac-like pulses of coherent electromagnetic energy similar to that depicted in FIG. 2. The solid line depicts a signal with a plurality of local amplitude maxima at various frequencies. These maxima are bounded by the decreasing amplitude of the signal produced with a single Dirac-like pulse. Further, the maxima exhibit a narrow bandwidth in their respective frequency ranges. A time separation between pulses may be chosen in such a manner as to improve or maximize the amplitude of the sonic energy signal within a specific frequency range.

Other desired ultrasonic signals may also be produced by a series of Dirac-like pulses and pulses of differing pulse widths. For example, a desired ultrasonic signal may also be produced by a toneburst followed by Dirac-like pulses.

In FIG. 3b, the dashed line denotes an ultrasonic energy signal produced by tone-burst of coherent electromagnetic energy. The solid line in FIG. 3b depicts an ultrasonic energy signal produced by a process using a single pulse having a width corresponding to one cycle of the tone-burst of coherent electromagnetic energy.

The advantage of using the single Dirac-like pulse of coherent electromagnetic energy is the higher amplitude of the produced signal. The sonic signal produced using the tone-burst of coherent electromagnetic energy has a relatively low amplitude.

The advantage of the series of Dirac-like pulses of coherent electromagnetic energy is the higher amplitude with narrow band width in several frequency ranges. The signal produced using the tone-burst of coherent electromagnetic energy and that signal produced using a single pulse with a width of one cycle of the toneburst of coherent electromagnetic energy are relatively lower in amplitude and broader in bandwidth. The series of Dirac-like pulses of coherent electromagnetic energy also produces significantly higher amplitude, narrow bandwidth signals in high frequency ranges.

The higher amplitude and narrow bandwidth allow better detection of the sonic energy signal because the SNR of the sonic energy signal is proportional to the amplitude and inversely proportional to the square root of the bandwidth of the sonic energy signal. The detection of sonic energy signals is, therefore, benefited by using the Dirac-like pulse method. This is because the Dirac-like pulse produces higher amplitude.

Detection of sonic energy signal is also benefited by using the series of Dirac-like pulses. This is because the series of Dirac-like pulses reduces the bandwidth within various detection frequency ranges while also producing the higher amplitude of the single Dirac-like pulse.

The higher amplitude and narrow bandwidth within various frequency ranges produced by the narrow pulses permits low SNR measurements to be taken in multiple frequency ranges. This greatly increases the amount of information that can be obtained from each measurement as there are more narrow bands from which measurement may be obtained. From each frequency range, a more accurate measurement can be acquired. Using multiple ranges, information confirming one attribute or simultaneous measurement of multiple attributes may be accomplished.

Figure 4:
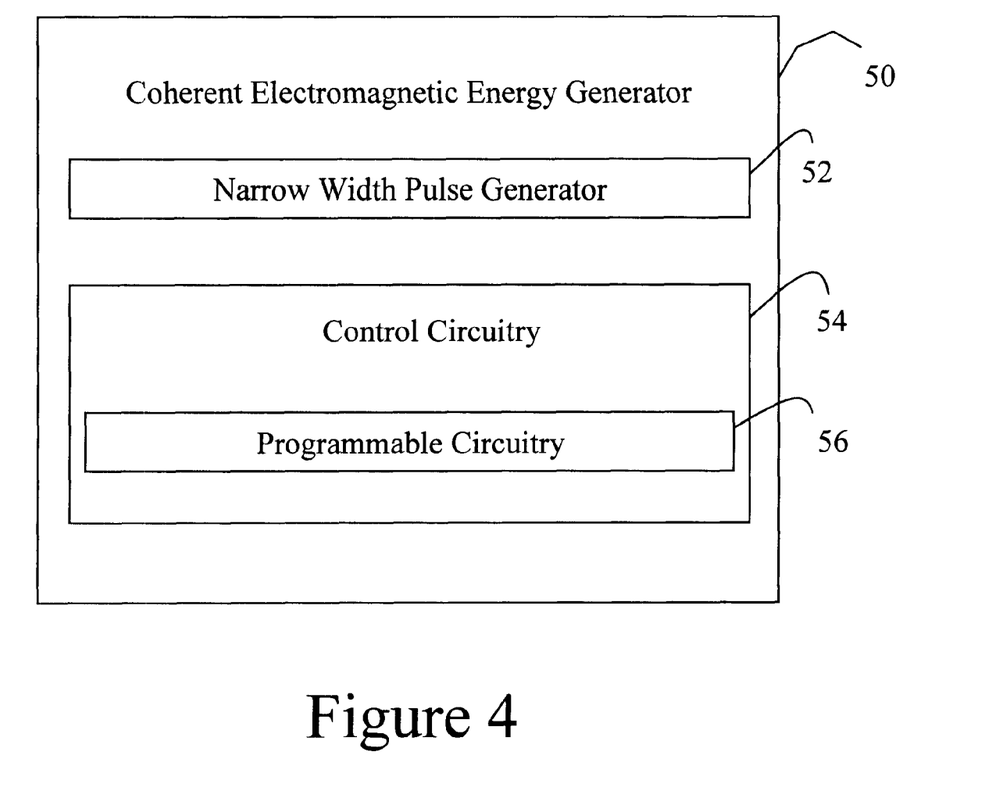
FIG. 4 is a schematic block diagram of an embodiment of a coherent electromagnetic energy generator which may be used in the system of FIG. 1.

FIG. 4 is a schematic block diagram of an embodiment of a coherent electromagnetic energy generator 50 which may be used in the system of FIG. 1. The coherent electromagnetic energy generator 50 has a pulse generator 52 and control circuitry 54. The pulse generator 52 and control circuitry 54 are in communication with the coherent electromagnetic energy generator 50. Programmable circuitry 56 is attached to the control circuitry 54. The pulse generator 52 and control circuitry 54 are, by way of example, depicted as being a part of the coherent electromagnetic energy generator 50 but may be separate.

The pulse generator 52 enables the coherent electromagnetic energy generator 50 to emit one or more narrow width pulses. The control circuitry 54 in communication with the coherent electromagnetic energy generator 50 controls the pulse widths of the one or more narrow width pulses.

The control circuitry 54 may perform in various ways. For example, the control circuitry 54 may determine a set of parameters used by the coherent electromagnetic energy generator 50 and/or pulse generator 52. Those parameters may manipulate the pulse widths and the time separation between pulses. The control circuitry 54 may then manipulate those parameters in the coherent electromagnetic energy generator 50 and/or the pulse generator 52 to optimize the ultrasonic signal generated by directing the manipulated the laser pulse at the manufactured object. The control circuitry may be implemented in several ways. These ways may include a computer or handheld circuitry that executes software instructions or implemented in hardware.

The programmable circuitry 56 is depicted, by way of example, as part of the control circuitry but may also be separate or may not be included in the system. The programmable circuitry 56 may aid the control circuitry 54 in determining the width of the one or more narrow pulses or the time difference between narrow width pulses. The programmable circuitry may be reprogrammed, adapted, and updated. For example, it may be reprogrammed using a handheld device, transferring a program across a network or wireless device, or by a direct device such as a keyboard, thus providing an adaptable system.

Figure 5:
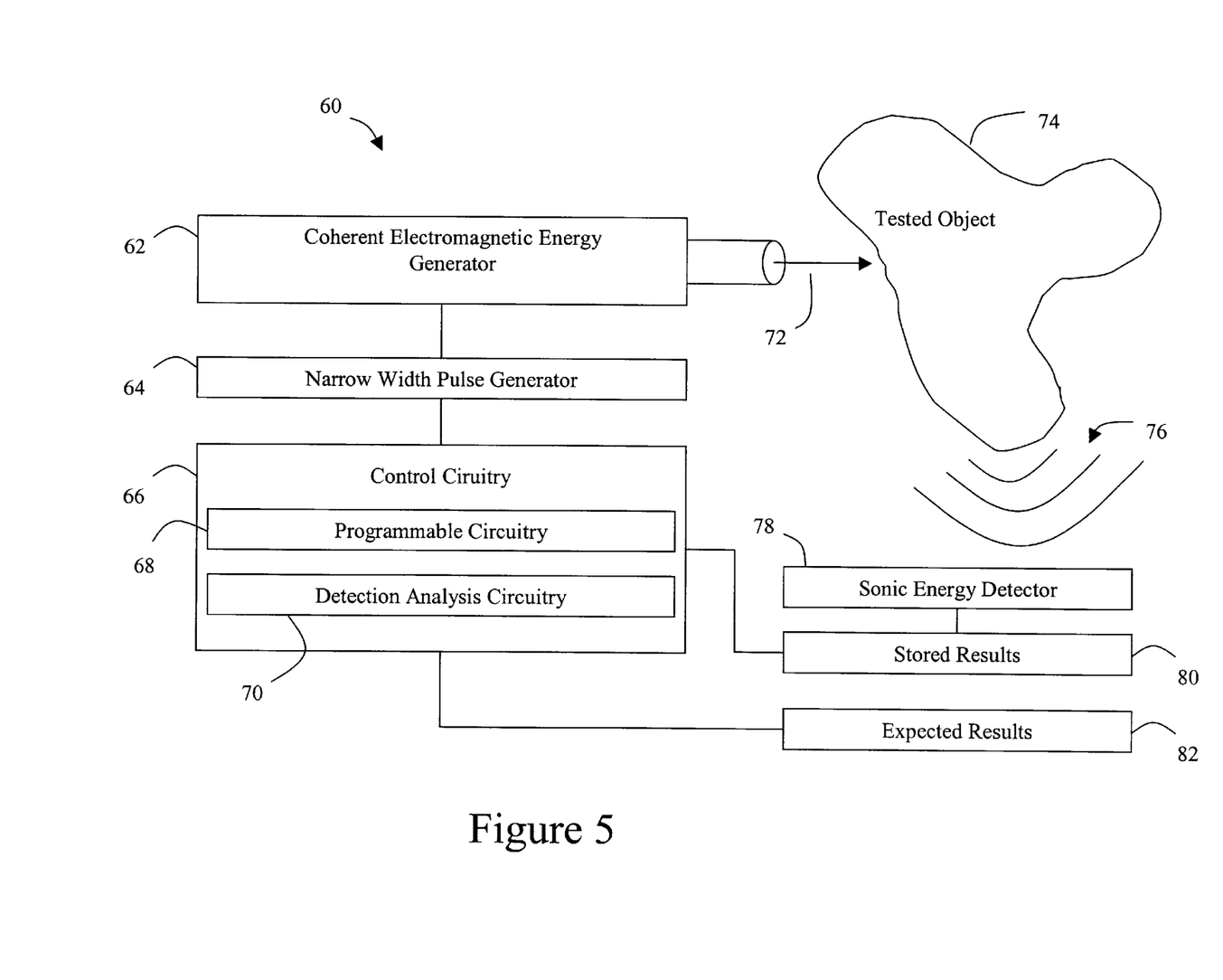
FIG. 5 is a schematic block diagram of an exemplary embodiment of the system of FIG. 1 represented in the context of laser ultrasound testing.

FIG. 5 is a schematic block diagram of an exemplary embodiment of the system of FIG. 1 represented in the context of laser ultrasound testing. A laser ultrasound testing device 60 has a coherent electromagnetic energy generator 62 coupled to a pulse generator 64. The pulse generator 64 and coherent electromagnetic energy generator 62 produce one or more Dirac-like pulses of coherent electromagnetic energy 72. The coherent electromagnetic energy generator 62 may be a laser such as a ruby laser, a carbon dioxide laser, or a Nd:YAG laser, to name but a few or any other device that can produce electromagnetic pulsed energy like, but not limited to, an optical parametric oscillator.

The one or more Dirac-like pulses of coherent electromagnetic energy 72 impart energy to the tested object 74. This energy effects a sonic energy signal 76. This sonic energy signal 76 is detected by a sonic energy detector 78.

A control circuitry 66 is shown. This control circuitry 66, by way of example, is depicted as separate from the coherent electromagnetic energy generator 62 but may be a part of the coherent electromagnetic energy generator 62. The control circuitry 66 is shown as in communication with the pulse generator 64. This control circuitry 66 may communicate with the pulse generator 64 or the coherent electromagnetic energy generator 62 coupled to the pulse generator 64. Through this communication, the control circuitry 66 may control the pulse widths of the one or more Dirac-like pulses of coherent electromagnetic energy 72 and the time difference between pulses in a series of Dirac-like pulses of coherent electromagnetic energy.

The control circuitry 66 may perform various functional aspects. For example, the control circuitry 66 may determine a set of parameters used by the coherent electromagnetic energy generator 62 and/or pulse generator 64. Those parameters may manipulate the pulse widths and the time separations between pulses. The control circuitry 66 may then manipulate those parameters in the coherent electromagnetic energy generator 62 and/or the pulse generator 64 to optimize the ultrasonic signal generated by directing the manipulated the laser pulses at the manufactured object.

A programmable circuitry 68 and a detection analysis circuitry 70 are attached to the control circuitry 66. By way of example, the programmable circuitry 68 and the detection analysis circuitry 70 are depicted as part of the control circuitry 66 but they may be separate. The detection analysis circuitry and programmable circuitry can be implemented on an as needed basis. The detection circuitry 70 may also be programmable.

A set of stored results 80 and a set of expected results 82 may be communicated to the detection circuitry 70. The stored results may also be coupled to the sonic energy detector 78. These stored results 80 may be a representation of the sonic energy signal detected by the sonic energy detector 78. The expected results 82 may be past results, calculated results, modeled results, or simulated results.

The detection analysis circuitry 70 compares the stored results 80 to the expected results 82 or may perform other calculations using the stored results 80. This detection analysis circuitry 70 may communicate with the programmable circuitry 68 and the control circuitry 66.

The control circuitry 66 may use information from the detection analysis circuitry 70, information from the programmable circuitry 68, or information known about the object 74, the coherent electromagnetic energy generator 62, or the pulse generator 64 to determine the pulse widths of the Dirac-like pulses of coherent electromagnetic energy 72. The control circuitry 66 may also use this information to determine the time difference between the Dirac-like pulses in a series of Dirac-like pulses of coherent electromagnetic energy. Other characteristics of the Dirac-like pulses such as power, temporal profile, beam shape, beam size, and frequency content may also be controlled. As such, a pulse may be defined to produce a particular sonic signal or response.

In this manner, the system can adaptively optimize the sonic response and improve the testing technique. This may produce more accurate and detailed testing. The improved testing may lead to advancing material research or early detection of flaws and defects. In an industry like the airline industry, advanced materials and early flaw detection could improve safety and prevent some catastrophic accidents.

Figure 6:
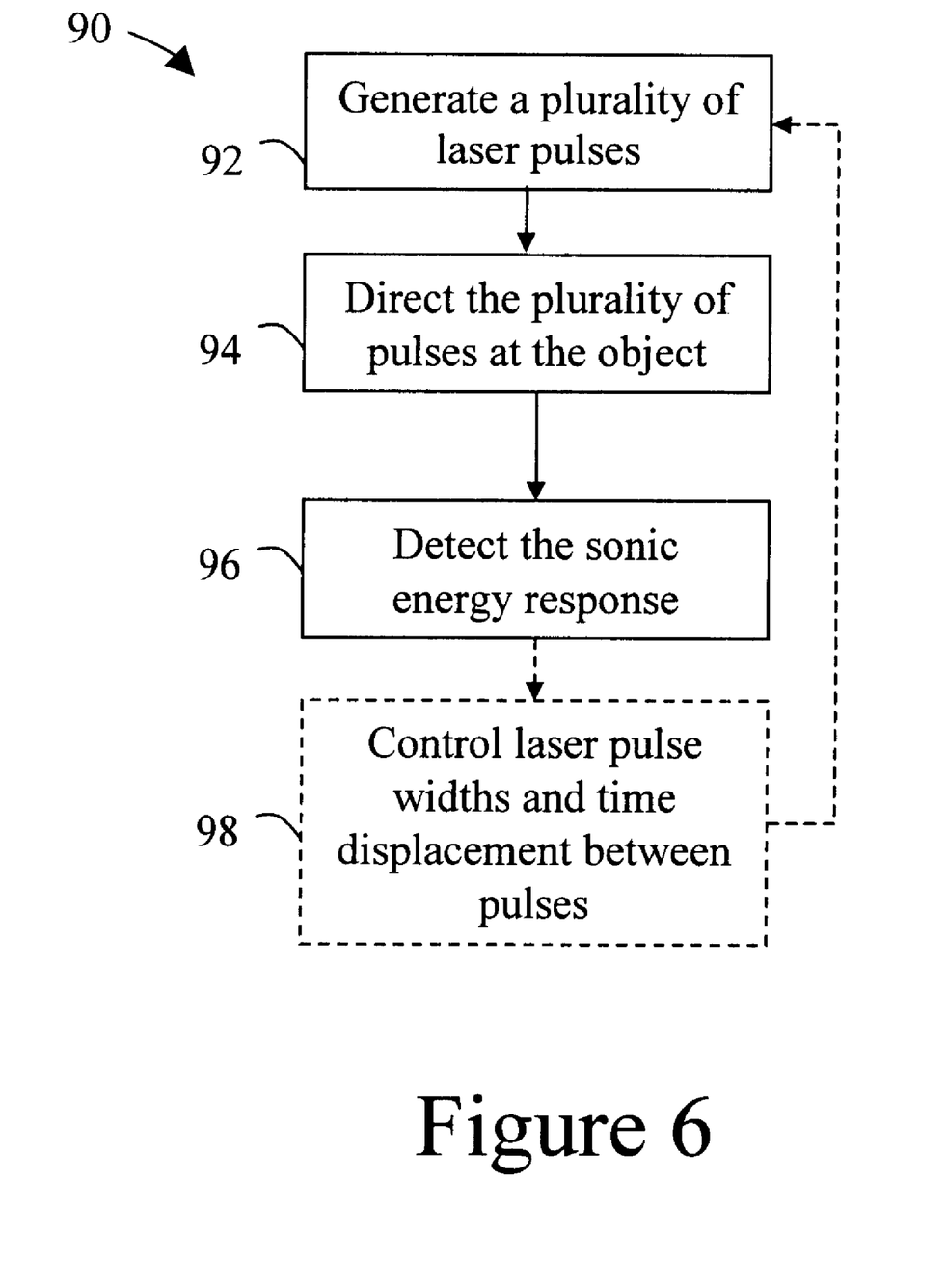
FIG. 6 is a flow diagram of an exemplary method that the system of FIG. 1 may use.

FIG. 6 is a flow diagram of an exemplary method that the system of FIG. 1 may use. In a block 92, the method comprises generating a plurality of narrow laser pulses. In a next block 94, the plurality of pulses are directed at a manufactured object. These pulses impart energy on or in the manufactured object. This energy initiates a sonic energy signal. In a block 96, the sonic energy signal is detected.

A pulse width, time separation between pulses, and other characteristics may be controlled by an additional step 98 if the detected sonic energy signal is not optimized. This step of controlling the pulse width and time separation 98 may use the detected sonic signal to determine the controlling action.

An alternate exemplary method may use a combination of long and narrow laser pulses. Another exemplary method may also include the step of generating a viewable form of the detected sonic energy signal.

Figure 7:
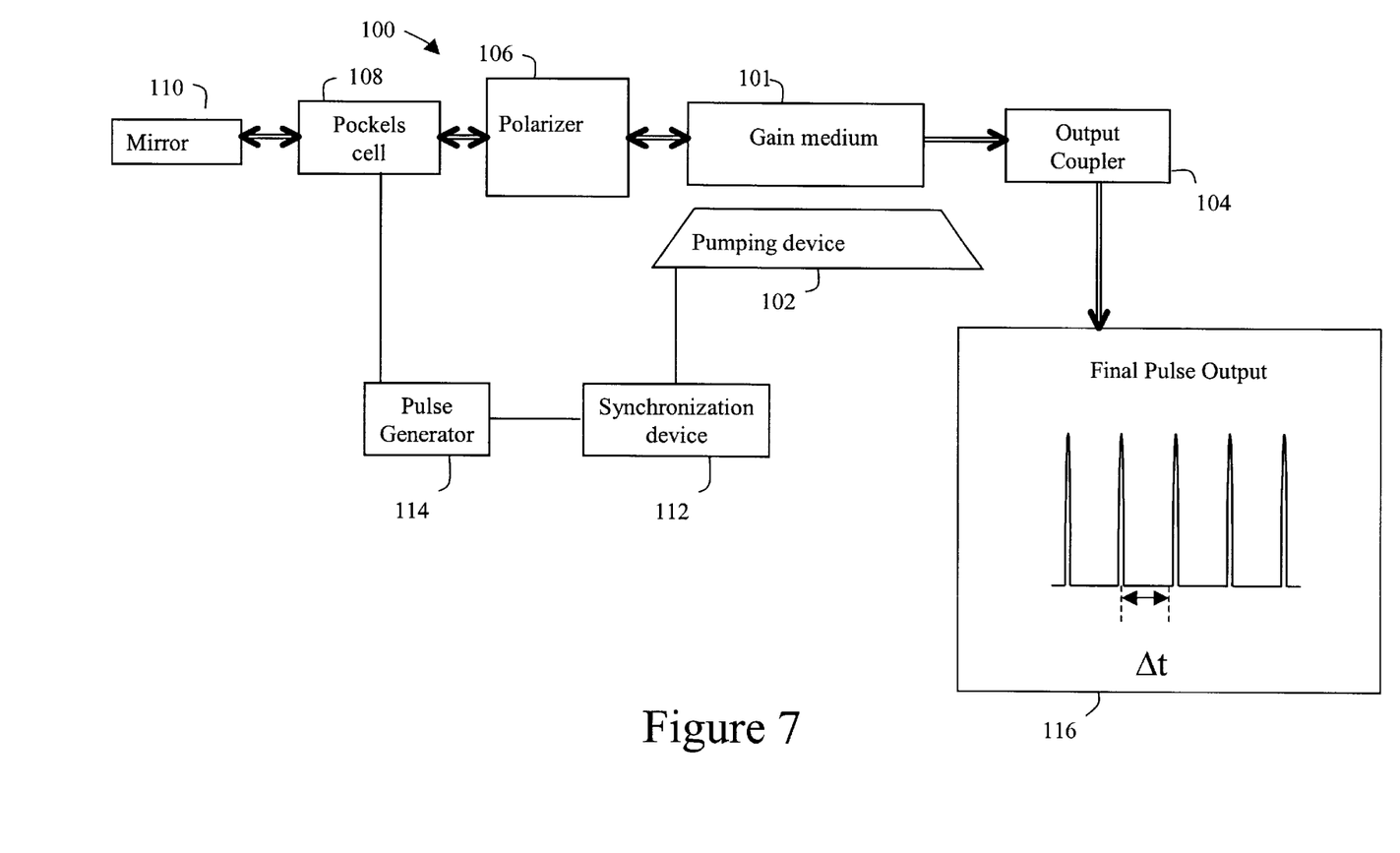
FIG. 7 is schematic diagram depicting an exemplary embodiment of an apparatus for producing the pulses of coherent electromagnetic energy of FIG. 2.

FIG. 7 is a schematic diagram depicting an exemplary embodiment of an apparatus 100 for producing the pulses of coherent electromagnetic energy of FIG. 2. The apparatus for producing the pulses has a gain medium 101, a pumping device 102, a synchronizing device 112, a pulse generator 114, a Pockels cell 108, a mirror 110, a polarizer 106, and an output coupler 104. The gain medium 101 is excited by the pumping device 102. The synchronization device 112 communicates with the pulse generator 114. The pulse generator 114 adjusts the Pockels cell 108 to permit photons to pass through the polarizer 106. These photons reflect off the mirror 110 and form a coherent beam of electromagnetic energy. This beam passes out through the output coupler 104. The coherent electromagnetic energy is depicted as a series of pulses in the final pulse output 116 and may be those pulses described above.

Figure 8:
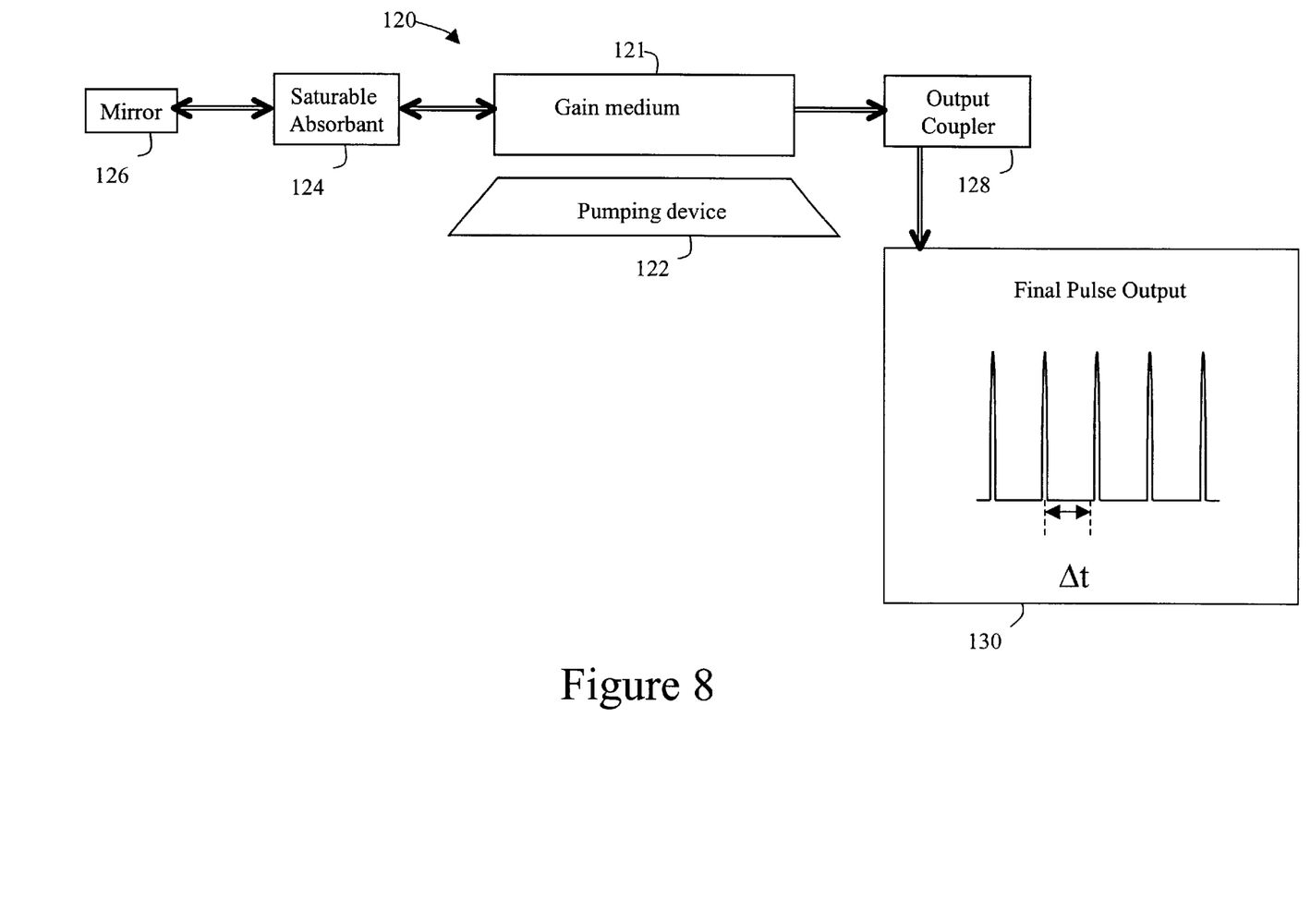
FIG. 8 is a schematic diagram depicting another exemplary embodiment of the apparatus for producing the pulses of coherent electromagnetic energy of FIG. 2.

FIG. 8 is a schematic diagram depicting another exemplary embodiment of an apparatus 120 for producing the pulses of coherent electromagnetic energy of FIG. 2. This apparatus has a gain medium 121, a pumping device 122, a saturable absorbent 124, a mirror 126, and an output coupler 128. The gain medium 121 is excited by the pumping device 122. The saturable absorbent 124 saturates with electromagnetic energy until it becomes effectively transparent, permitting electromagnetic energy to pass through. This electromagnetic energy reflects off a mirror 126 and passes out through an output coupler 128. In this manner, the electromagnetic energy forms a beam of coherent electromagnetic energy. The coherent electromagnetic energy is depicted as a series of pulses in the final pulse output 130 and may be those pulses described above.

Figure 9:
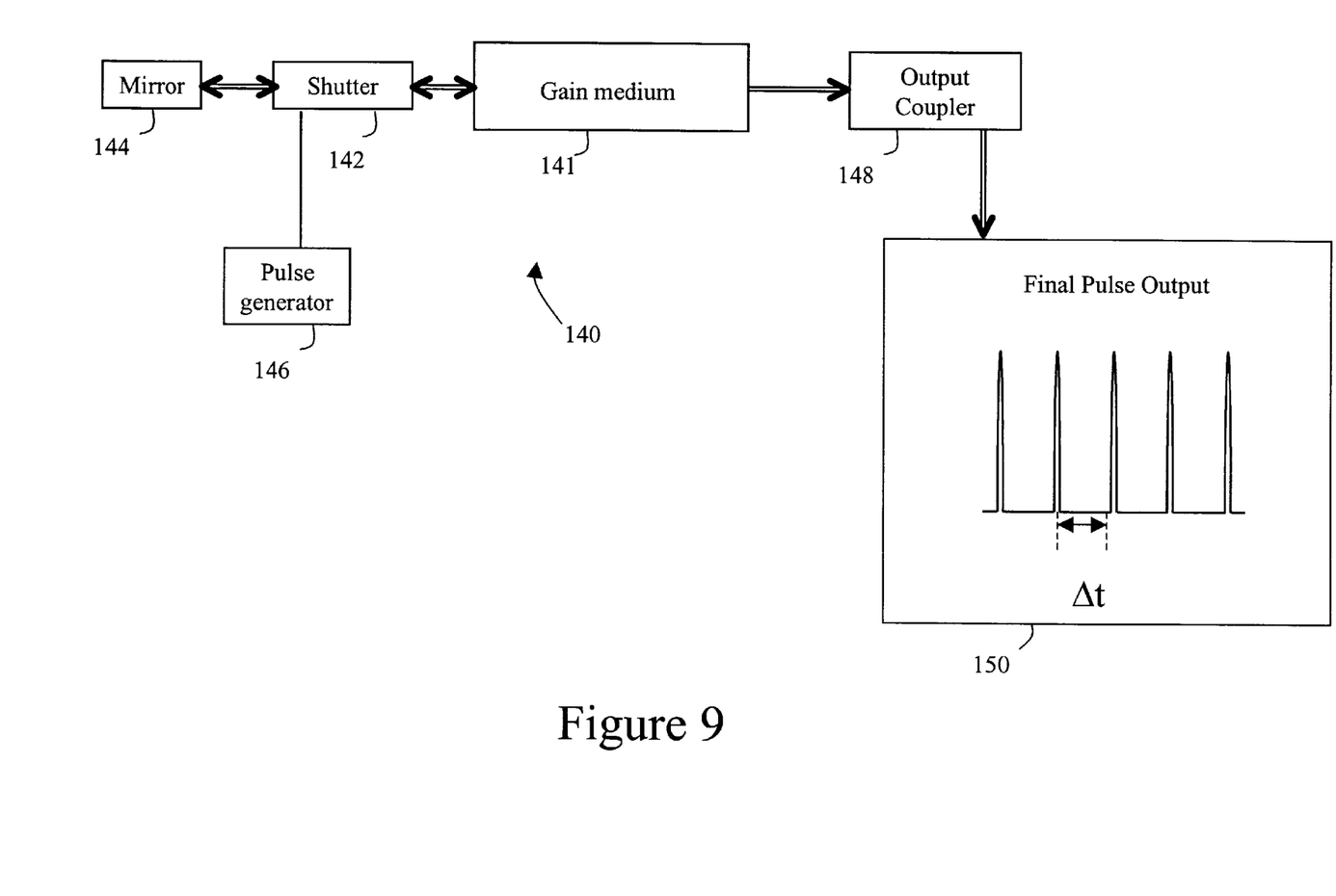
FIG. 9 is another schematic diagram depicting an exemplary embodiment of the apparatus for producing the pulses of coherent electromagnetic energy of FIG. 2.

FIG. 9 is another schematic diagram depicting an exemplary embodiment of an apparatus 140 for producing the pulses of coherent electromagnetic energy of FIG. 2. An excited gain medium 141 passes electromagnetic energy through a shutter 142 when the shutter is directed to open by a pulse generator 146. The electromagnetic energy reflects off a mirror 144 and passes out through an output coupler 148. In this manner, the electromagnetic energy forms a beam of coherent electromagnetic energy. The coherent electromagnetic energy is depicted as a series of pulses in the final pulse output 150 and may be those pulses described above.

FIG. 10 is a schematic diagram depicting a further exemplary embodiment of an apparatus 160 for producing the pulses of coherent electromagnetic energy of FIG. 2. The apparatus has an excited gain medium 161, a front mirror 166, a back mirror 162, an acoustooptic cell 168, and a third mirror 164. Electromagnetic energy 170 from the excited gain medium 161 reflects off the front mirror 166 and the back mirror 162. When permitted, the electromagnetic energy passes through the acoustooptic cell 168. This electromagnetic energy then reflects off a third mirror 164, passes back through the acoustooptic cell and reflects off the back mirror 162. In this manner, the electromagnetic energy forms a beam of coherent electromagnetic energy. The coherent electromagnetic energy is depicted as a series of pulses in the final pulse output 172 and may be those pulses described above.

Figure 11:
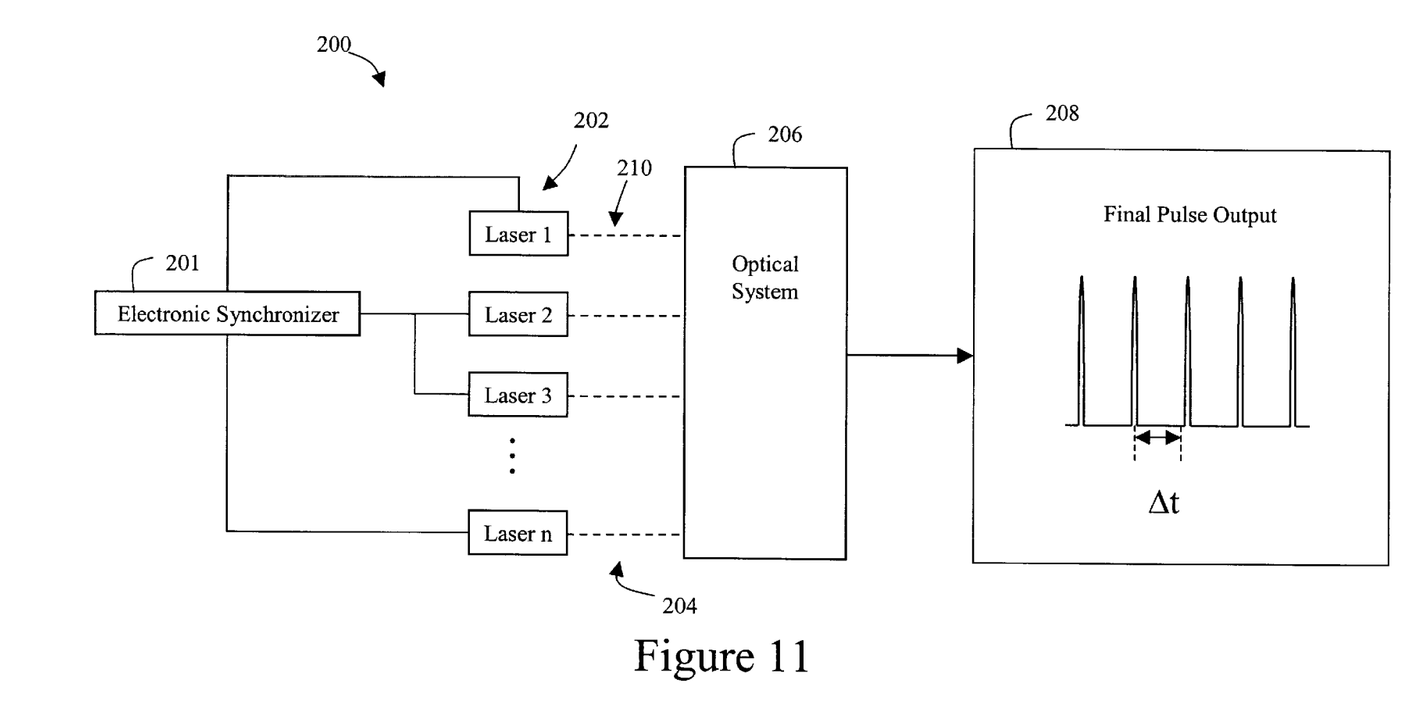
FIG. 11 is a further schematic diagram depicting another exemplary embodiment of the apparatus for producing the pulses of coherent electromagnetic energy of FIG. 2.

FIG. 11 is a further schematic diagram depicting another exemplary embodiment of an apparatus 200 for producing the pulses of coherent electromagnetic energy of FIG. 2. An electronic synchronizer 201 synchronizes an output of an array of lasers 202 to produce an array of beams of coherent electromagnetic energy 204. This array of beams 204 is then transmitted to an optical system 206. The array of beams 204 may be transmitted through many means 210. These means 210 may include mirrors or fiber optical cables, to name but a couple. The array of beams 204 is then combined in the optical system 206 to form a coherent electromagnetic energy pulse. The coherent electromagnetic energy pulse is depicted as a series of pulses in the final pulse output 208 and may be those pulses described above.

As such, a device and method for testing a physical attribute of a manufactured object is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims that follow.

We claim:

1. A method for testing a physical attribute of a manufactured object, the method comprising:
   generating a plurality of coherent electromagnetic energy pulses;
   the pulses having a time separation between the end of a pulse and the beginning of a successive pulse;
   the plurality of pulses having pulse widths of less than 20% the time separation;
   directing the plurality of pulses at the manufactured object;
   the pulses imparting energy on or in the manufactured object;
   the energy initiating a sonic energy signal;
   dynamically controlling one or both of the pulse width of a next pulse and the time separation between pulses;
   controlling the width of the next coherent electromagnetic energy pulse and the time separation between pulses based upon the physical attribute of the manufactured object; and
   measuring the sonic energy signal.

2. The method of claim 1, wherein the step of measuring is performed by a laser interferometer device.

3. The method of claim 1, wherein the step of measuring is performed by one or more piezoelectric transducers.

4. The method of claim 1, wherein the step of measuring is performed by electromagnetic transducer.

5. The method of claim 1, wherein the step of measuring is performed by a gas-coupled laser acoustic detector.

6. The method of claim 1, the method further comprising:
   controlling the width of the next coherent electromagnetic energy pulse and the time separation between pulses based upon a feature of the coherent electromagnetic energy pulse selected from the group consisting of wavelength, frequency, power, beam projected shape, temporal profiles and energy amplitude.

7. A system for testing a physical attribute of a manufactured object, the system comprising;
   at least one coherent electromagnetic energy generator;
   a pulse generator coupled to the at least one coherent electromagnetic energy generator which produces coherent electromagnetic energy pulses;
   the pulses having a time separation between the end of a pulse and the beginning of a successive pulse;
   the pulses having pulse widths of less than 20% the time separation;
   the pulses imparting energy on or in the manufactured object;
   the energy initiating a sonic energy signal;
   a controlling circuitry controlling the width of the coherent electromagnetic energy pulses, wherein said controlling circuitry controls the width of the coherent electromagnetic energy pulses based upon the physical attribute of the manufactured object; and
   a sonic energy detector that detects the sonic energy signal.

8. The system of claim 7, the system further comprising:
   said detector being a laser interferometer.

9. The system of claim 7, the system further comprising:
   said detector being one or more piezoelectric transducers on the surface of the object.

10. The system of claim 7, the system further comprising:
    said detector being a gas-coupled laser acoustic detector.

11. The system of claim 7, the system further comprising:
    said detector being one or more electromagnetic transducers.

12. The system of claim 7, the system further comprising:
    said controlling circuitry controlling the width of the coherent electromagnetic energy pulse based upon a feature of the coherent electromagnetic energy pulse selected from the group consisting of wavelength, frequency, power, beam projected shape, temporal profiles and energy amplitude.

13. A method for testing a physical attribute of a manufactured object, the method comprising:
    generating a plurality of Dirac laser pulses, the laser pulses having a time separation between a pulse and a successive pulse;
    dynamically controlling one or both of the pulse width of a next pulse and the time separation between pulses;
    controlling the width of the next coherent electromagnetic energy pulse and the time separation between pulses based upon the physical attribute of the manufactured object.
    directing the plurality of laser pulses at the manufactured object;
    the laser pulses imparting energy on or in the manufactured object;
    the energy initiating a sonic energy signal; and
    measuring the sonic energy signal.

14. The method of claim 13, wherein the step of measuring is performed by a laser interferometer device.

15. The method of claim 13, wherein the step of measuring is performed by one or more piezoelectric transducers.

16. The method of claim 13, wherein the step of measuring is performed by a gas-coupled laser acoustic detector.

17. The method of claim 13, wherein the step of measuring is performed by electromagnetic transducer.

18. The method of claim 13, the method further comprising:
    controlling the width of the next coherent electromagnetic energy pulse and the time separation between pulses based upon a feature of the coherent electromagnetic energy pulse selected from the group consisting of wavelength, frequency, power, beam projected shape, temporal profiles and energy amplitude.

19. A system for testing a physical attribute of a manufactured object, the system comprising;
    at least one laser generator;
    a pulse generator coupled to the at least one laser generator which produces a plurality of Dirac laser pulses;
    the laser pulses having a time separation from a pulse to a successive pulse;
    the laser pulses imparting energy on or in the manufactured object;
    the energy initiating a sonic energy signal;

a controlling circuitry which controls one or both of the pulse widths of the plurality of laser pulses and the time separations between pulses, said controlling circuitry controlling the width of the next coherent electromagnetic energy pulse and the time separation between pulses based upon the physical attribute of the manufactured object; and a sonic energy detector that detects the sonic energy signal.

20. A system for testing a physical attribute of a manufactured object, the system comprising;

at least one laser generator;

a pulse generator coupled to the at least one laser generator which produces a plurality of Dirac laser pulses;

the laser pulses having a time separation from a pulse to a successive pulse;

the laser pulses imparting energy on or in the manufactured object;

the energy initiating a sonic energy signal;

a controlling circuitry which controls one or both off the pulse widths of the plurality of laser pulses and the time separations between pulses, said controlling circuitry controlling the width of the next coherent electromagnetic energy pulse and the time separation between pulses based upon a feature of the coherent electromagnetic energy pulse selected from the group consisting of wavelength, frequency, power, beam projected shape, temporal profiles and energy amplitude; and a sonic energy detector that detects the sonic energy signal.

* * * * *

UNITED STATES PATENT AND TRADEMARK OFFICE
CERTIFICATE OF CORRECTION

PATENT NO.   : 6,668,654 B2  Page 1 of 1
DATED        : December 30, 2003
INVENTOR(S)  : Marc Dubois, Peter Lorraine and Robert Filkins It is certified that error appears in the above-identified patent and that said Letters Patent is hereby corrected as shown below:

Column 5,
Line 34, delete "," and insert -- and --.

Column 12,
Line 4, delete "off" and insert -- of --.

Signed and Sealed this

Twenty-ninth Day of November, 2005

JON W. DUDAS
*Director of the United States Patent and Trademark Office*